(12) United States Patent
Fuchikami et al.

(10) Patent No.: US 7,470,808 B2
(45) Date of Patent: Dec. 30, 2008

(54) METHOD FOR PRODUCING FLUORINE-CONTAINING ACRYLATE

(75) Inventors: Takamasa Fuchikami, Tsukuba (JP); Noriko Wakasa, Sagamihara (JP); Kenji Tokuhisa, Shunan (JP); Hideyuki Mimura, Shunan (JP); Shoji Arai, Shunan (JP)

(73) Assignees: Tosoh F-Tech, Inc., Shunan-shi (JP); Sagami Chemical Research Center, Ayase-shi (JP)

( * ) Notice: Subject to any disclaimer, the term of this patent is extended or adjusted under 35 U.S.C. 154(b) by 0 days.

(21) Appl. No.: 10/550,387

(22) PCT Filed: Mar. 24, 2004

(86) PCT No.: PCT/JP2004/004017

§ 371 (c)(1),
(2), (4) Date: Nov. 2, 2005

(87) PCT Pub. No.: WO2004/085374

PCT Pub. Date: Oct. 7, 2004

(65) Prior Publication Data

US 2006/0122423 A1 Jun. 8, 2006

(30) Foreign Application Priority Data

Mar. 26, 2003 (JP) ............................ 2003-085164

(51) Int. Cl.
*C07C 69/63* (2006.01)
*C07C 67/36* (2006.01)
*C07C 69/66* (2006.01)

(52) U.S. Cl. .................. 560/227; 560/207; 560/184; 560/187

(58) Field of Classification Search ................ 560/227, 560/184, 187, 207; 562/520
See application file for complete search history.

(56) References Cited

U.S. PATENT DOCUMENTS 4,855,487 A 8/1989 Fuchikami et al.

FOREIGN PATENT DOCUMENTS

| JP | 58-154529 | 9/1983 |
| JP | 63-152342 | 6/1988 |
| JP | 8-104661 | 4/1996 |

OTHER PUBLICATIONS

Ugo Matteoli et al., "Esters and N, N-dialkylamides of 2-(trifluoromethyl)acrylic acid (TFMAA) through Pd-catalysed carbonylation of fluorinated unsaturated substrates", Journal of Molecular Catalysis A: Chemical, 143, pp. 287-295, 1999.

*Primary Examiner*—Daniel M Sullivan
*Assistant Examiner*—Jennifer Y Cho
(74) *Attorney, Agent, or Firm*—Wenderoth, Lind & Ponack, LLP.

(57) ABSTRACT

A process for producing a fluorine-containing acrylic acid ester represented by $CH_2=C(Rf)(COOR)$ characterized in that 1-bromo-1-perfluoroalkylethene represented by $CH_2=CBr-Rf$, or 1,2-dibromo-1-perfluoroalkylethane represented by $CH_2CBr-CHBr-Rf$ is allowed to react with an alcohol represented by ROH in the presence of a palladium catalyst, carbon monoxide, and two or more kinds of bases. The fluorine-containing acrylic acid ester is a useful compound having wide applications in materials for pharmaceuticals and functional polymers.

5 Claims, No Drawings

METHOD FOR PRODUCING FLUORINE-CONTAINING ACRYLATE

TECHNICAL FIELD

The present invention relates to a process for producing a fluorine-containing acrylic acid ester which is a useful compound widely used as materials and the like for pharmaceuticals and functional polymers.

BACKGROUND ART

Conventionally, the following methods have been known for producing a fluorine-containing acrylic acid ester.

(1) A method in which α-(trifluoromethyl)acrylic acid is allowed to react with thionyl chloride to render it α-(trifluoromethyl)acrylyl chloride, which is then reacted with a fluorine-containing alcohol in the presence of a base to generate α-(trifluoromethyl)acrylic acid ester (Patent document 1).

(2) A method in which α-(trifluoromethyl)acrylic acid is allowed to react with a fluorine-containing alcohol or methanol in the presence of fuming sulfuric acid to generate α-(trifluoromethyl)acrylic acid ester (Patent document 2).

(3) A method in which 2-bromo-3,3,3-trifluoropropene is allowed to react with ethanol in the presence of palladium catalyst, carbon monoxide, and triethylamine single base (Patent document 3).

However, the method (1) has such a drawback that the yield of converting reaction into α-(trifluoromethyl)acrylyl chloride is low, and an anhydride is generated as a byproduct. The method (2) has such a drawback that use of a great amount of hard-to-handle fuming sulfuric acid is necessary. The method (3) has such a drawback that alkoxy fluorine-containing propionic acid ester is produced as a main product. In this patent document, we can find the description "1,1,1-trifluoro-2,3-dihalopropane may be used while directly converted into 2-halo-3,3,3-trifluoropropene within the system" but not a practical example for reaction with alcohol. Also, the fact that reaction in the presence of two or more kinds of bases will improve the yield of fluorine-containing acrylic acid ester has never been known (see Comparative examples).

(Patent document 1) Japanese Examined Patent Publication No. Hei 3-8329

(Patent document 2) Japanese Patent Laid-Open Publication No. Sho 60-42352

(Patent document 3) Japanese Patent Laid-Open Publication No. Sho 58-154529

DISCLOSURE OF THE INVENTION

It is an object of the present invention to provide a process for producing a fluorine-containing acrylic acid ester by which many drawbacks accompanying the conventional arts as described above are overcome, and which realizes simplicity and high versatility.

The inventors of the present application diligently searched for solution for the drawbacks accompanying the conventional approaches as described above, and found a simple, versatile and highly selective process for producing a fluorine-containing acrylic acid ester using 1-bromo-1-perfluoroalkylethene or 1,2-dibromo-1-perfluoroalkylethane as a starting material, and finally accomplished the present invention.

Specifically, the present invention provides a process for producing a fluorine-containing acrylic acid ester represented by the general formula (IV):

(wherein, Rf represents a perfluoroalkyl group and R represents an unsubstituted or substituted alkyl group), wherein 1-bromo-1-perfluoroalkylethene represented by the general formula (I):

(wherein Rf is as defined above), or 1,2-dibromo-1-perfluoroalkylethane represented by the general formula (II):

(wherein Rf is as defined above) is allowed to react with an alcohol represented by the general formula (III):

ROH     (III)

(wherein R is as defined above) in the presence of a palladium catalyst, carbon monoxide, and two or more kinds of bases.

BEST MODE FOR CARRYING OUT THE INVENTION

The "alkyl group" used in the present invention refers to a straight, branched, or cyclic alkyl group having 1 to 20, preferably 1 to 15 carbon(s) optionally having a substituent not involved in the reaction. Examples of such alkyl groups include methyl group, ethyl group, propyl group, isopropyl group, butyl group, t-butyl group, 1-methylpropyl group, 2-methylpropyl group, pentyl group, 1,1-dimethylpropyl group, 1,2-dimethylpropyl group, 2,2-dimethylpropyl group, 1-methylbutyl group, 2-methylbutyl group, 3-methylbutyl group, cyclopropyl group, cyclobutyl group, 1-methylpentyl group, dimethylcyclopropyl group, methylcyclobutyl group, cyclopentyl group, hexyl group, cyclohexyl group, 3-methylcyclohexyl group, 4-1-methylpentyl group, methylcyclohexyl group, heptyl group, octyl group, cyclohexylmethyl group, 1-cyclohexylethyl group, cyclooctyl group, 3-hydroxy-1-adamantyl group, 1,3-adamantanediyl group, nonyl group, decyl group, 1-menthyl group, 1-adamantyl group, 2-adamantyl group, 2-methyl-2-adamantyl group, 2-ethyl-2-adamantyl group, 2-propyl-2-adamantyl group, 2-butyl-2-adamantyl group, norbornyl group, bicyclo[2,2,2]octyl group, bicyclo[3,2,1]octyl group, 2,2,2-trifluoroethyl group, 4,4,4-trifluorobutyl group, 2-methoxyethyl group, and benzyl group.

The "perfluoroalkyl group" used in the present invention refers to a straight, branched, or cyclic fluorinated alkyl group having 1 to 20, preferably 1 to 10 carbon(s). Examples of such fluorinated alkyl groups include trifluoromethyl group, perfluoroethyl group, perfluoropropyl group, perfluoro isopropyl group, perfluorobutyl group, perfluoro-sec-butyl group, perfluoro-tert-butyl group, perfluoro isopentyl group, perfluorohexyl group, perfluoro octyl group, perfluoro decyl group, and the like, with perfluoro alkyl groups having 1 to 4 carbon(s) being preferred, and trifluoromethyl group being more preferred.

The present invention is conducted in the presence of a palladium catalyst. Examples of the palladium catalyst that can be used include metal palladiums such as palladium black and palladium sponge; supported palladium such as palladium/carbon, palladium/alumina, palladium/asbestos, palladium/barium sulfate, palladium/barium carbonate, palladium/calcium carbonate, and palladium/polyethylene amine; palladium salts such as palladium chloride, palladium bromide, palladium iodide, palladium acetate, palladium trifluoroacetate, palladium nitrate, palladium oxide, palladium sulfate, palladium cyanate, allyl palladium chloride dimmer, and palladium acetyl acetate; palladium complex salts and complex compounds such as sodium hexachloro palladate, potassium hexachloro palladate, sodium tetrachloro palladate, potassium tetrachloro palladate, potassium tetrabromo palladate, tetra(acetonitrile)palladium fluoroborate, ammonium tetrachloro palladate, ammonium hexachloro palladate, dichloro bis(acetonitrile)palladium, dichloro bis(benzonitrile)palladium, and tris(dibenzylidene acetone)dipalladium; amine-based complexes such as dichlorodiamine palladium, palladium tetraamine nitrate, tetraamine palladium tetrachloro palladate, dichlorodipyridine palladium, dichloro(2,2'-bipyridyl)palladium, dichloro(4,4'-dimethyl-2,2'-bipyridyl)palladium, dichloro(phenanthroline)palladium, (phenanthroline)palladium nitrate, dichloro(tetramethyl phenanthroline)palladium, (tetramethyl phenanthroline)palladium nitrate, diphenanthroline palladium nitrate, and bis (tetramethyl phenanthroline) palladium nitrate; phosphine-based complexes such as dichloro bis(triphenylphosphine) palladium, dichloro bis(tricyclohexylphosphine)palladium, tetrakis (triphenylphosphine)palladium, dichloro[1,2-bis (diphenylphosphino)ethane]palladium, dichloro[1,3-bis (diphenylphosphino)propane]palladium, dichloro[1,4-bis (diphenylphosphino)butane]palladium, and dichloro[1,1'-bis (diphenylphosphino)ferrocene]palladium.

In the cases of amine-based complexes or phosphine-based complexes, they may be prepared in a reaction system by adding a ligand to a precursor palladium compound. Examples of the ligand for the amine-based complexes that can be used for preparation in a system include ammonia, diethylamine, triethylamine, 1,2-bis(dimethylamino)ethane, 1,2-bis(diphenyamino)ethane, 1,2-bis(dimethylamino)propane, 1,3-bis(dimethylamino)propane, pyridine, aminopyridine, dimethylaminopyridine, 2,2'-bipyridyl, 4,4'-dimethyl-2,2'-bipyridyl, 2,2'-biquinoline, phenanthroline, tetramethyl phenanthroline, and the like.

Examples of the ligand for phosphine-based complex that can be used for preparation in a system include triphenylphosphine, tricyclohexylphosphine, tri-t-butylphosphine, 1,2-bis (diphenylphosphino)ethane, 1,3-bis(diphenylphosphino) propane, 1,4-bis(diphenylphosphino)butane, 1,1'-bis (diphenylphosphino)ferrocene, sodium diphenylphosphinobenzene-3-sulfonate, tricyclohexylphosphine, tri(2-furyl)phosphine, tris(2,6-dimethoxyphenyl) phosphine, tris(4-methoxyphenyl)phosphine, tris(4-methylphenyl)phosphine, tris(3-methylphenyl)phosphine, tris(2-methylphenyl)phosphine, and the like.

These palladium catalysts may be used in a so-called catalytic amount, which is selected in the range of about 0.0001 to 0.1 equivalent, usually in the range of about 0.001 to 0.05 equivalent, relative to 1-bromo-1-perfluoroalkyllethene represented by the general formula (I) or 1,2-dibromo-1-perfluoroalkylethane represented by the general formula (II).

The alcohol represented by the general formula (III) is a straight, branched, or cyclic aliphatic alcohol having 1 to 20 carbon(s), optionally having a substituent not involved in the reaction. Examples of the alcohol include methanol, ethanol , propanol, butanol, pentanol, hexanol, octanol, cyclohexylethanol, 2-propanol, 2-methyl-2-propanol, 2-butanol, 2-hexanol, 2-methyl-1-propanol, cyclopentanol, cyclohexanol, cyclooctanol, 3-methylcyclohexanol, 4-methylcyclohexanol, cyclohexyl methanol, benzylalcohol, 2,2,2-trifluoroethanol, ethyleneglycolmonomethylether, 1-menthol, 1-adamantanol, 2-methyl-2-adamantanol, 2-ethyl-2-adamantanol, 2-butyl-2-adamantanol, 1,3-adamantanediol, and 2-norbornanol. Such an alcohol may be used in an amount which is equivalent or large excess to 1,2-dibromo-1-perfluoroalkylethane represented by the general formula (I), and the alcohol may also serve as a solvent. Usually, it may be used in an amount ranging from 1 to 5 equivalent(s).

In the process of the present invention, the reaction is conducted under the pressure of carbon monoxide. The reaction method is not particularly limited, and it may be carried out in a batch or semi-batch manner. The carbon monoxide pressure is usually selected from the range of 0.1 to 10 MPaG, however, about 0.5 to 5 MPaG is preferable in respect of reaction efficiency from the view points of safety and economy.

The present invention is conducted in the presence of two or more kinds of bases, and preferably, at least one kind from these two or more kinds of bases is an inorganic base, an inorganic salt or an organometallic compound, and preferably, at least one kind of base is amines.

Examples of the inorganic salt that can be used include alkaline metal alkoxides such as sodium methoxide, sodium ethoxide, sodium t-butoxide, potassium methoxide, potassium ethoxide, and potassium t-butoxide; alkaline earth metal alkoxides such as magnesium diethoxide and magnesium dimethoxide; and anion exchange resins.

Examples of the inorganic salt that can be used include alkaline metal hydrides such as lithium hydride, sodium hydride and potassium hydride; alkaline earth metal hydrides such as beryllium hydride, magnesium hydride, and calcium hydride; alkaline metal hydroxides such as lithium hydroxide, sodium hydroxide, and potassium hydroxide; alkaline earth metal hydroxides such as beryllium hydroxide, magnesium hydroxide, and calcium hydroxide; alkaline metal carbonates such as lithium carbonate, sodium carbonate, and potassium carbonate; and alkaline earth metal carbonates such as beryllium carbonate, magnesium carbonate, and calcium carbonate.

Examples of the organometallic compound that can be used include organic alkaline metal compounds such as butyl lithium, t-butyl lithium, phenyl lithium, triphenylmethyl sodium, and ethyl sodium; and organic alkaline earth metal compounds such as methylmagnesium bromide, dimethylmagnesium, phenylmagnesium chloride, phenylcalcium bromide, and bis(dicyclobentadiene)calcium.

Examples of the amines that can be used include tertiary amines such as trimethylamine, triethylamine, tributylamine, N,N-dimethylaniline, dimethylbenzylamine, and N,N,N',N'-tetramethyl-1,8-naphthalenediamine; and heteroaromatic amines such as pyridine, pyrrole, uracil, collidine, and lutidine.

In respect of two or more kinds of bases used in the present invention, bases combining an inorganic base, an inorganic salt, or an organometallic compound with amines are preferred from the view points of reaction yield efficiency, and selectivity.

The inorganic base, the inorganic salt, or the organometallic compound is preferably used in such an amount that at least one kind has a molar ratio of 0.001 to 1, relative to the compound represented by the general formula (I) or (II) from the view point of yield, reaction efficiency and selectivity.

The use amount of amines may be selected in the range of from molar ratio of 1 to large excess to the compound represented by the general formula (I) or (II), and usually about 1 to 8 equivalent(s).

In practicing the present invention, the alcohol represented by the general formula (III) may serves also as a solvent, and it is preferred to use a solvent that is inert to reactions. Examples of the solvent that can be used include aromatic solvents such as benzene, toluene, and xylene; hydrocarbon solvents such as hexane and octane; and polar solvents such as acetone, acetonitrile, acetone, sulfolane, tetrahydrofuran, dioxane, dimethoxyethane, diglyme, dimethylsulfoxide, N,N-dimethylformamide, N,N-dimethylacetoamide, N-methylpyrrolidone, 1,3-dimethyl-2-imidazolidinone, and hexamethyl phosphoryl triamide. The use amount of the solvent is not particularly limited insofar as a part or a whole of materials is dissolved at a reaction temperature.

The reaction temperature may be appropriately selected in the range of from room temperature to 300° C., however, the range from 50° C. to 160° C. is preferred from the view point of reaction efficiency.

EXAMPLES

In the following, the present invention will be described in more detail by way of examples and comparative examples, however the present invention is not limited by these examples.

Example 1

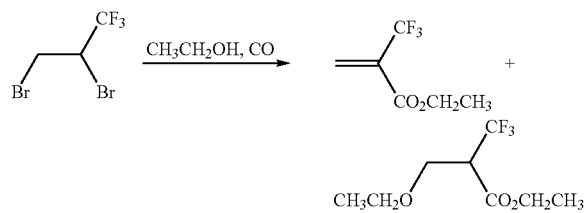

An autoclave was charged with 2,3-dibromo-1,1,1-trifluoropropane (0.2559 g, 1.0 mmol), ethanol (0.057 g, 1.24 mmol), triethylamine (0.202 g, 2.0 mmol), 60%-sodium hydride (0.0080 g, 0.2 mmol), dichlorobis(triphenylphosphine) palladium (II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F-NMR integration value revealed that 2-trifluoromethyl acrylic acid ethyl ester was obtained with a yield of 74.9% on the basis of 2,3-dibromo-1,1,1-trifluoropropane standard. Also 5.1% of 3-ethoxy-2-(trifluoromethyl)propionic acid ethyl ester was obtained.

2-trifluoromethyl acrylic acid ethyl ester $^{19}$F—NMR (250 MHz, CDCl$_3$, δ ppm): −65.9 (t, J=1.50 Hz)

GC-MS MS (EI): m/z 169 (M$^+$+1), 123 (100%)

3-ethoxy-2-(trifluoromethyl)propionic acid ethyl ester $^{19}$F—NMR (250 MHz, CDCl$_3$, δ ppm): −66.8 (d, J=8.52 Hz)

Comparative Example 1

An autoclave was charged with 2,3-dibromo-1,1,1-trifluoropropane (0.2559 g, 1.0 mmol), ethanol (0.057 g, 1.24 mmol), triethylamine (0.223 g, 2.2 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid ethyl ester was obtained with a yield of 64.6% on the basis of 2,3-dibromo-1,1,1-trifluoropropane. Also 13.2% of 3-ethoxy-2-(trifluoromethyl)propionic acid ethyl ester Example 2

An autoclave was charged with 2,3-dibrom-6-1,1,1-trifluoropropane (0.2559 g, 1.0 mmol), ethanol (0.057 g, 1.24 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid ethyl ester was obtained with a yield of 81.6% on the basis of 2,3-dibromo-1,1,1-trifluoropropane. Also, 3.0% of 3-ethoxy-2-(trifluoromethyl)propionic acid ethyl ester was obtained.

Example 3

An autoclave was charged with 2,3-dibromo-1,1,1-trifluoropropane (0.2559 g, 1.0 mmol), ethanol (0.057 g, 1.24 mmol), triethylamine (0.202 g, 2.0 mmol), lithium carbonate (0.0074 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid ethyl ester was obtained with a yield of 84.7% on the basis of 2,3- dibromo-1,1,1-trifluoropropane. Also 2.8% of 3-ethoxy-2-(trifluoromethyl)propionic acid ethyl ester was obtained.

Example 4

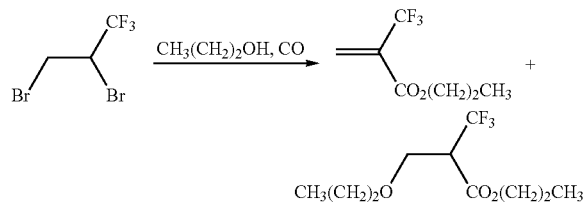

An autoclave was charged with 2,3-dibromo-1,1,1-trifluoropropane (0.2559 g, 1.0 mmol), 1-propanol (0.072 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid propyl ester was obtained with a yield of 80.2% on the basis of 2,3-dibromo-1,1,1-trifluoropropane. Also, 3.8% of 3-propoxy-2-(trifluoromethyl)propionic acid propyl ester was obtained.

2-trifluoromethyl acrylic acid propyl ester
$^{19}F$—NMR (250 MHz, CDCl$_3$, δ ppm): −65.8 (t, J=1.52 Hz)
GC-MS MS (CI): m/z 183 (M$^+$+1)

3-propoxy-2-(trifluoromethyl)propionic acid propyl ester
$^{19}F$—NMR (250 MHz, CDCl$_3$, δ ppm): −66.7 (d, J=8.53 Hz)

Comparative Example 2

An autoclave was charged with 2,3-dibromo-1,1,1-trifluoropropane (0.2559 g, 1.0 mmol), 1-propanol (0.072 g, 1.2 mmol), triethylamine (0.223 g, 2.2 mmol), dichlorobis(triphenylphosphine)palladium(II) (0.0070 g, 0.01 mmol), and tetrahydrofuran (2.0 mL), which were then stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid propyl ester was obtained with a yield of 65.4% on the basis of 2,3-dibromo-1,1,1-trifluoropropane. Also 8.9% of 3-propoxy-2-(trifluoromethyl)propionic acid propyl ester was obtained.

Example 5

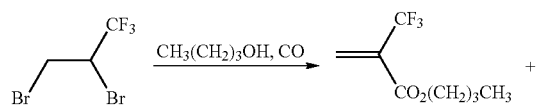

-continued

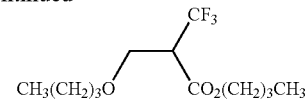

An autoclave was charged with 2,3-dibromo-1,1,1-trifluoropropane (0.2559 g, 1.0 mmol), 1-butanol (0.089 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid butyl ester was obtained with a yield of 82.6% on the basis of 2,3-dibromo-1,1,1-trifluoropropane. Also 3.5% of 3-butoxy-2-(trifluoromethyl)propionic acid butyl ester was obtained.

2-trifluoromethyl acrylic acid butyl ester
$^{19}F$—NMR (250 MHz, CDCl$_3$, δ ppm): −65.7 (t, J=1.48 Hz)
GC-MS MS (CI): m/z 197 (M$^+$+1)

3-butoxy-2-(trifluoromethyl)propionic acid butyl ester
$^{19}F$—NMR (250 MHz, CDCl$_3$, δ ppm): −66.7 (d, J=8.53 Hz)

Comparative Example 3

An autoclave was charged with 2,3-dibromo-1,1,1-trifluoropropane (0.2559 g, 1.0 mmol), 1-butanol (0.089 g, 1.2 mmol), triethylamine (0.223 g, 2.2 mmol), dichlorobis(triphenylphosphine)palladium(II) (0.0070 g, 0.01 mmol), and tetrahydrofuran (2.0 mL), which were stirred at 120° C. for 5 hours after introducing carbon monoxide (1.0 MPaG) After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid butyl ester was obtained with a yield of 68.7% on the basis of 2,3-dibromo-1,1,1-trifluoropropane. Also 9.3% of 3-butoxy-2-(trifluoromethyl)propionic acid butyl ester was obtained.

Example 6

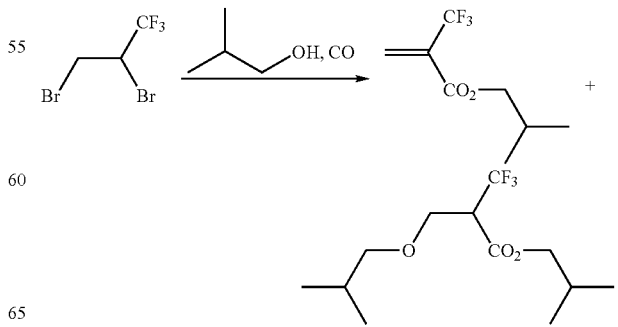

An autoclave was charged with 2,3-dibromo-1,1,1-trifluoropropane (0.2559 g, 1.0 mmol), 2-methyl-1-propanol (0.089 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and toluene (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methyl-1-propyl ester was obtained with a yield of 82.0% on the basis of 2,3-dibromo-1,1,1-trifluoropropane. Also 3.1% of 3-(2-methyl-1-propyloxy)-2-(trifluoromethyl)propionic acid 2-methyl-1-propyl ester was obtained.

2-trifluoromethyl acrylic acid 2-methyl-1-propyl ester
$^{19}$F—NMR (250 MHz, CDCl$_3$, δ ppm): −65.8 (t, J=1.48 Hz)
GC-MS MS (CI): m/z 197 (M$^+$+1)

3-(2-methyl-1-propyloxy)-2-(trifluoromethyl)propionic acid 2-methyl-1-propyl ester
$^{19}$F—NMR (250 MHz, CDCl$_3$, δ ppm): −66.7 (d, J=8.52 Hz)

Comparative Example 4

An autoclave was charged with 2,3-dibromo-1,1,1-trifluoropropane (0.2559 g, 1.0 mmol), 2-methyl-1-propanol (0.089 g, 1.2 mmol), triethylamine (0.223 g, 2.2 mmol), dichlorobis(triphenylphosphine)palladium(II) (0.0070 g, 0.01 mmol), and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methyl-1-propyl ester was obtained with a yield of 65.1% on the basis of 2,3-dibromo-1,1,1-trifluoropropane. Also 9.2% of 3-(2-methyl-1-propyloxy)-2-(trifluoromethyl)propionic acid 2-methyl-1-propyl ester was obtained.

Example 7

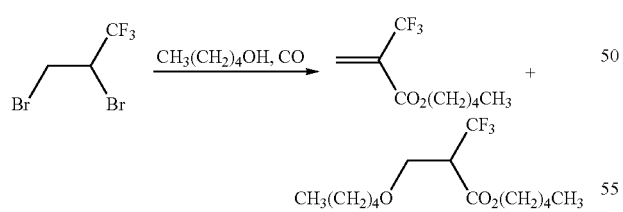

An autoclave was charged with 2,3-dibromo-1,1,1-trifluoropropane (0.2559 g, 1.0 mmol), 1-pentanol (0.106 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and toluene (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid pentyl ester was obtained with a yield of 84.0% on the basis of 2,3-dibromo-1,1,1-trifluoropropane. Also 4.5% of 3-pentyloxy-2-(trifluoromethyl)propionic acid pentyl ester was obtained.

2-trifluoromethyl acrylic acid pentyl ester
$^{19}$F—NMR (250 MHz, CDCl$_3$, δ ppm): −65.7 (t, J=1.51 Hz)
GC-MS MS (CI): m/z 211 (M$^+$+1)

3-pentyloxy-2-(trifluoromethyl)propionic acid pentyl ester
$^{19}$F—NMR (250 MHz, CDCl$_3$, δ ppm): −66.8 (d, J=8.45 Hz)

Comparative Example 5

An autoclave was charged with 2,3-dibromo-1,1,1-trifluoropropane (0.2559 g, 1.0 mmol), 1-pentanol (0.106 g, 1.2 mmol), triethylamine (0.223 g, 2.2 mmol), dichlorobis(triphenylphosphine)palladium(II) (0.0070 g, 0.01 mmol), and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid pentyl ester was obtained with a yield of 72.3% on the basis of 2,3-dibromo-1,1,1-trifluoropropane. Also 11.0% of 3-pentyloxy-2-(trifluoromethyl)propionic acid pentyl ester was obtained.

Example 8

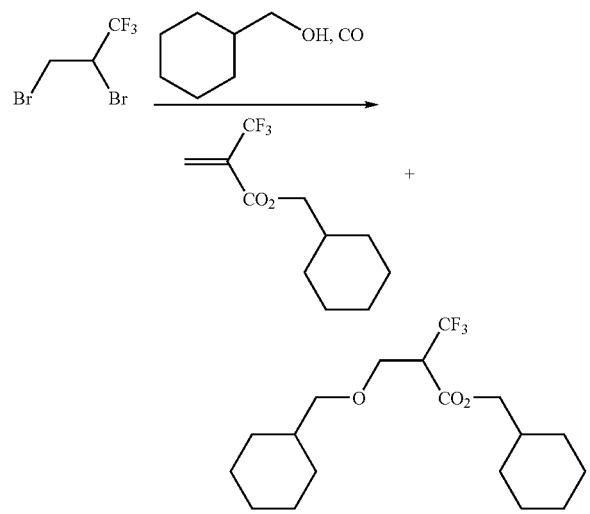

An autoclave was charged with 2,3-dibromo-1,1,1-trifluoropropane (0.2559 g, 1.0 mmol), cyclohexyl methanol (0.137 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid cyclohexylmethyl ester was obtained with a yield of 80.7% on the basis of 2,3-dibromo-1,1,1-trifluoropropane. Also 4.4% of 3-cyclohexylmethyloxy-2-(trifluoromethyl)propionic acid cyclohexylmethyl ester was obtained.

2-trifluoromethyl acrylic acid cyclohexylmethyl ester
$^{19}$F-NMR (250 MHz, CDCl$_3$, δ ppm): −65.7 (t, J=1.46 Hz)
GC-MS MS (CI): m/z 237 (M$^+$+1)

3-cyclohexylmethyloxy-2-(trifluoromethyl)propionic acid cyclohexylmethyl ester
$^{19}$F—NMR (250 MHz, CDCl$_3$, δ ppm): −66.7 (d, J=8.54 Hz)

Comparative Example 6

An autoclave was charged with 2,3-dibromo-1,1,1-trifluoropropane (0.2559 g, 1.0 mmol), cyclohexyl methanol (0.137 g, 1.2 mmol), triethylamine (0.223 g, 2.2 mmol), dichlorobis(triphenylphosphine)palladium(II) (0.0070 g, 0.01 mmol) and tetrahydrofuran (2.0 mL), which were stirred at 120° C. for 5 hours after introducing carbon monoxide (1.0 MPaG) After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid cyclohexylmethyl ester was obtained with a yield of 66.9% on the basis of 2,3-dibromo-1,1,1-trifluoropropane. Also 11.3% of 3-cyclohexylmethyloxy-2-(trifluoromethyl)propionic acid cyclohexylmethyl ester was obtained.

Example 9

Quantification using a $^{19}$F—NMR integration value revealed that 2-trifluoromethyl acrylic acid benzyl ester was obtained with a yield of 71.7% on the basis of 2,3-dibromo-1,1,1-trifluoropropane. Also 7.8% of 3-benzyloxy-2-(trifluoromethyl)propionic acid benzyl ester was obtained.

2-trifluoromethyl acrylic acid benzyl ester
$^{19}$F—NMR (250 MHz, CDCl$_3$, δ ppm): −65.8 (t, J=1.34 Hz)
GC-MS MS (CI): m/z 231 (M$^+$+1)

3-benzyloxy-2-(trifluoromethyl)propionic acid benzyl ester
$^{19}$F—NMR (250 MHz, CDCl$_3$, δ ppm): −66.5 (d, J=8.36 Hz)

Comparative Example 7

An autoclave was charged with 2,3-dibromo-1,1,1-trifluoropropane (0.2559 g, 1.0 mmol), benzyl alcohol (0.119 g, 1.1 mmol), triethylamine (0.223 g, 2.2 mmol), dichlorobis(triphenylphosphine)palladium(II) (0.0070 g, 0.01 mmol) and tetrahydrofuran (2.0 mL), which were then stirred at 120° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid benzyl ester was obtained with a yield of 48.2% on the basis of 2,3-dibromo-1,1,1-trifluoropropane. Also 4.5% of 3-benzyloxy-2-(trifluoromethyl)propionic acid benzyl ester was obtained.

Example 10

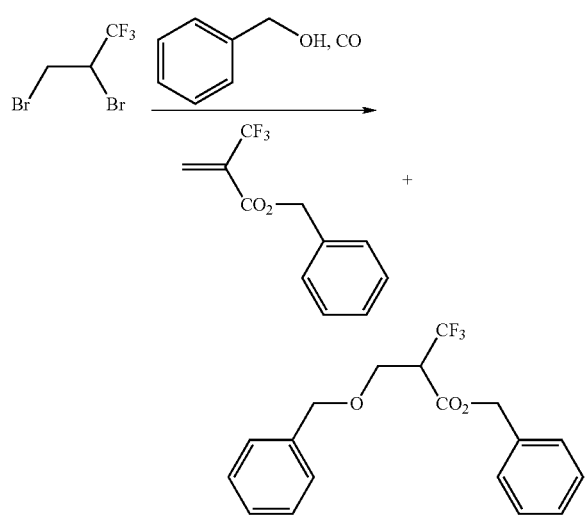

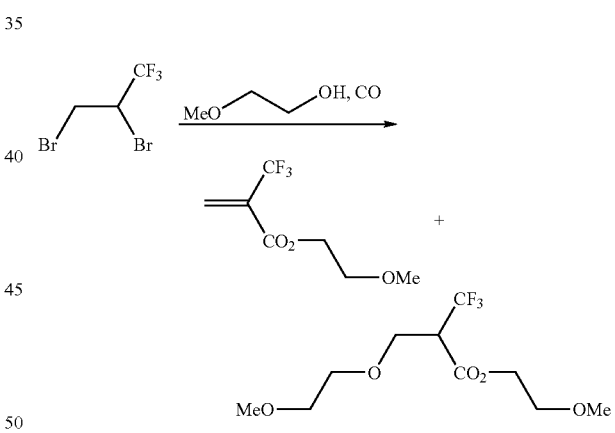

An autoclave was charged with 2,3-dibromo-1,1,1-trifluoropropane (0.2559 g, 1.0 mmol), benzyl alcohol (0.130 g, 1.2 mmol), triethylamine (0.202 g, 2.0 mmol), lithium carbonate (0.0148 g, 0.2 mmol), dichlorobis(triphenylphosphine)palladium(II) (0.0070 g, 0.01 mmol), and tetrahydrofuran (2.0 mL), which were stirred at 120° C. for 5 hours after introducing carbon monoxide (1.0 MPaG) After the end of the reaction, the autoclave was cooled, ventilated, and added with benzotrifluoride as an internal standard substance, followed by stirring and leaving still for a while to let a salt precipitate.

An autoclave was charged with 2,3-dibromo-1,1,1-trifluoropropane (0.2559 g, 1.0 mmol), 2-methoxyethanol (0.091 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methoxyethyl ester was obtained with a yield of 74.8% on the basis of 2,3-dibromo-1,1,1-trifluoropropane. Also 4.8% of 3-(2-methoxyethyloxy)-2-(trifluoromethyl)propionic acid 2-methoxyethyl ester was obtained.

2-trifluoromethyl acrylic acid 2-methoxyethyl ester $^{19}$F—NMR (250 MHz, CDCl$_3$, δ ppm): −65.9 (t, J=1.44 Hz)

GC-MS MS (CI): m/z 199 (M$^+$+1)

3-(2-methoxyethyloxy)-2-(trifluoromethyl)propionic acid 2-methoxyethyl ester $^{19}$F—NMR (250 MHz, CDCl$_3$, δ ppm): −66.7 (d, J=8.45 Hz)

Comparative Example 8

An autoclave was charged with 2,3-dibromo-1,1,1-trifluoropropane (0.2559 g, 1.0 mmol), 2-methoxyethanol (0.091 g, 1.2 mmol), triethylamine (0.223 g, 2.2 mmol), dichlorobis(triphenylphosphine)palladium(II) (0.0070 g, 0.01 mmol), and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methoxyethyl ester was obtained with a yield of 68.6% on the basis of 2,3-dibromo-1,1,1-trifluoropropane. Also 9.9% of 3-(2-methoxyethyloxy)-2-(trifluoromethyl)propionic acid 2-methoxyethyl ester was obtained.

Example 11

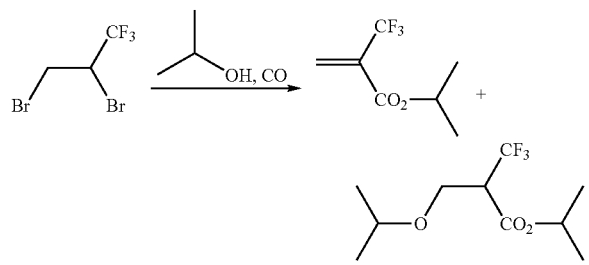

An autoclave was charged with 2,3-dibromo-1,1,1-trifluoropropane (0.2559 g, 1.0 mmol), 2-propanol (0.072 g, 1.2 mmol), triethylamine (0.202 g, 2.0 mmol), 60%-sodium hydride (0.0080 g, 0.2 mmol), dichlorobis(triphenylphosphine)palladium(II) (0.0070 g, 0.01 mmol) and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-propyl ester was obtained with a yield of 70.9% on the basis of 2,3-dibromo-1,1,1-trifluoropropane. Also 1.2% of 3-(2-propyloxy)-2-(trifluoromethyl)propionic acid 2-propyl ester was obtained.

2-trifluoromethyl acrylic acid 2-propyl ester $^{19}$F—NMR (250 MHz, CDCl$_3$, δ ppm): −65.9 (t, J=1.48 Hz)

GC-MS MS (EI): m/z 167 (M$^+$-Me, 13), 123 (100%)

MS(CI): m/z 183 (M$^+$+1)

3-(2-propyloxy)-2-(trifluoromethyl)propionic acid 2-propyl ester $^{19}$F—NMR (250 MHz, CDCl$_3$, δ ppm): −66.8 (d, J=8.52 Hz)

Comparative Example 9

An autoclave was charged with 2,3-dibromo-1,1,1-trifluoropropane (0.2559 g, 1.0 mmol), 2-propanol (0.072 g, 1.2 mmol), triethylamine (0.223 g, 2.2 mmol), dichlorobis(triphenylphosphine)palladium(II) (0.0070 g, 0.01 mmol) and tetrahydrofuran (2.0 mL), which were stirred at 120° C. for 5 hours after introducing carbon monoxide (1.0 MPaG) After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-propyl ester was obtained with a yield of 53.1% on the basis of 2,3-dibromo-1,1,1-trifluoropropane. Also 3.7% of 3-(2-propyloxy)-2-(trifluoromethyl)propionic acid 2-propyl ester was obtained.

Example 12

An autoclave was charged with 2,3-dibromo-1,1,1-trifluoropropane (0.2559 g, 1.0 mmol), 2-propanol (0.072 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-propyl ester was obtained with a yield of 83.0% on the basis of 2,3-dibromo-1,1,1-trifluoropropane. Also 0.8% of 3-(2-propyloxy)-2-(trifluoromethyl)propionic acid 2-propyl ester was obtained.

Example 13

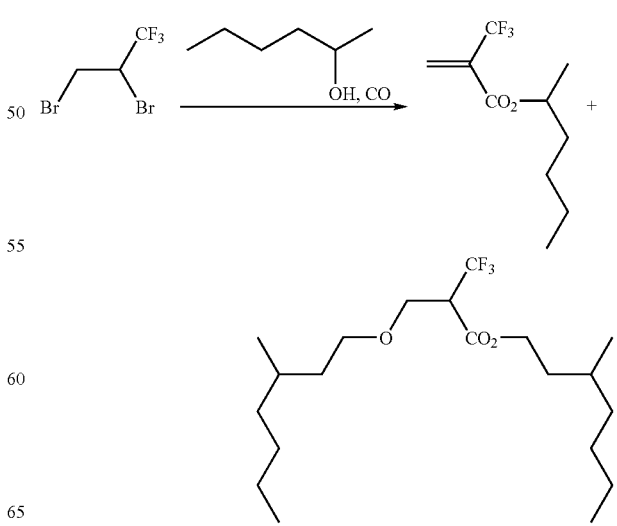

An autoclave was charged with 2,3-dibromo-1,1,1trifluoropropane (0.2559 g, 1.0 mmol), 2-hexanol (0.123 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 1-methylpentyl ester was obtained with a yield of 84.0% on the basis of 2,3-dibromo-1,1,1-trifluoropropane. Also 0.9% of 3-(1-methylpentyloxy)-2-(trifluoromethyl)propionic acid 1-methylpentyl ester was obtained.

2-trifluoromethyl acrylic acid 1-methylpentyl ester
$^{19}$F—NMR (250 MHz, CDCl$_3$, δ ppm): −65.8 (t, J=1.41 Hz)
GC-MS MS (CI): m/z 225 (M$^+$+1)

3-(1-methylpentyloxy)-2-(trifluoromethyl)propionic acid 1-methylpentyl ester
$^{19}$F—NMR (250 MHz, CDCl$_3$, δ ppm): −66.72 (d, J=8.52 Hz), −66.74 (d, J=8.61 Hz), −66.78 (d, J=8.65 Hz), −66.79 (d, J=8.59 Hz)

Comparative Example 10

An autoclave was charged with 2,3-dibromo-1,1,1-trifluoropropane (0.2559 g, 1.0 mmol), 2-hexanol (0.123 g, 1.2 mmol), triethylamine (0.223 g, 2.2 mmol), dichlorobis(triphenylphosphine)palladium(II) (0.0070 g, 0.01 mmol), and tetrahydrofuran (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 1-methylpentyl ester was obtained with a yield of 72.9% on the basis of 2,3-dibromo-1,1,1-trifluoropropane. Also 4.8% of 3-(1-methylpentyloxy)-2-(trifluoromethyl)propionic acid 1-methylpentyl ester was obtained.

Example 14

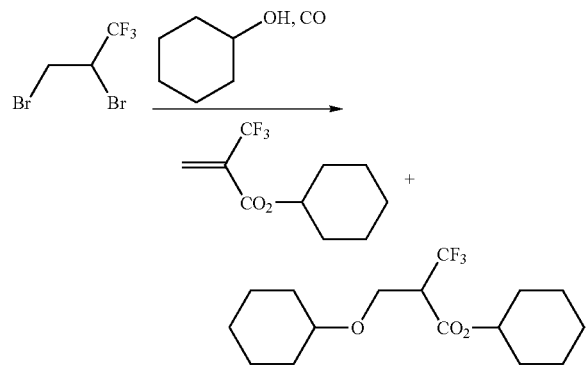

An autoclave was charged with 2,3-dibromo-1,1,1-trifluoropropane (0.2559 g, 1.0 mmol), cyclohexanol (0.120 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and toluene (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid cyclohexyl ester was obtained with a yield of 80.5% on the basis of 2,3-dibromo-1,1,1-trifluoropropane. Also 1.2% of 3-cyclohexyloxy-2-(trifluoromethyl)propionic acid cyclohexyl ester was obtained.

2-trifluoromethyl acrylic acid cyclohexyl ester
$^{19}$F—NMR (250 MHz, CDCl$_3$, δ ppm): −65.8 (t, J=1.48 Hz)
GC-MS MS (CI): m/z 223 (M$^+$+1)

3-cyclohexyloxy-2-(trifluoromethyl)propionic acid cyclohexyl ester
$^{19}$F—NMR (250 MHz, CDCl$_3$, δ ppm): −66.8 (d, J=8.52 Hz)

Comparative Example 11

An autoclave was charged with 2,3-dibromo-1,1,1-trifluoropropane (0.2559 g, 1.0 mmol), cyclohexanol (0.120 g, 1.2 mmol), triethylamine (0.223 g, 2.2 mmol), dichlorobis(triphenylphosphine)palladium(II) (0.0070 g, 0.01 mmol), and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid cyclohexyl ester was obtained with a yield of 73.4% on the basis of 2,3-dibromo-1,1,1-trifluoropropane. Also 5.3% of 3-cyclohexyloxy-2-(trifluoromethyl)propionic acid cyclohexyl ester was obtained.

Example 15

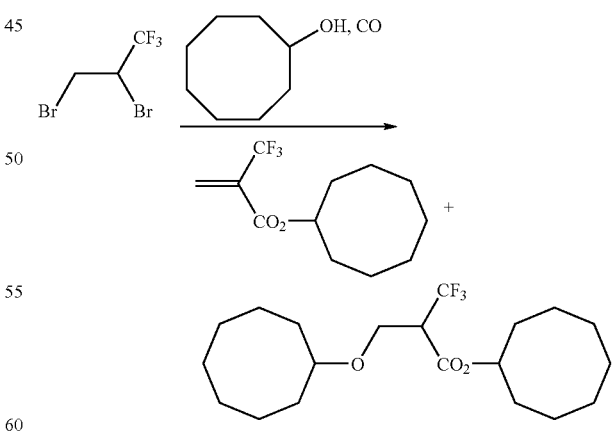

An autoclave was charged with 2,3-dibromo-1,1,1-trifluoropropane (0.2559 g, 1.0 mmol), cyclooctanol (0.154 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and toluene (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt to precipitate. Quantification using a $^{19}$F—NMR integration value revealed that 2-trifluoromethyl acrylic acid cyclooctyl ester was obtained with a yield of 83.7% on the basis of 2,3-dibromo-1,1,1-trifluoropropane.

2-trifluoromethyl acrylic acid cyclooctyl ester
$^{19}$F—NMR (250 MHz, CDCl$_3$, δ ppm): −65.9 (t, J=1.48 Hz)
GC-MS MS (CI): m/z 249 (M$^+$−1)

Comparative Example 12

An autoclave was charged with 2,3-dibromo-1,1,1-trifluoropropane (0.2559 g, 1.0 mmol), cyclooctanol (0.154 g, 1.2 mmol), triethylamine (0.223 g, 2.2 mmol), dichlorobis(triphenylphosphine)palladium(II) (0.0070 g, 0.01 mmol), and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt to precipitate., Quantification using a $^{19}$F—NMR integration value revealed that 2-trifluoromethyl acrylic acid cyclooctyl ester was obtained with a yield of 72.3% on the basis of 2,3-dibromo-1,1,1-trifluoropropane. Also 5.2% of 3-cyclohexyloxy-2-(trifluoromethyl)propionic acid cyclohexyl ester was obtained.

3-cyclooctyloxy-2-(trifluoromethyl)propionic acid cyclooctyl ester
$^{19}$F—NMR (250 MHz, CDCl$_3$, δ ppm): −66.7 (d, J=8.52 Hz)

Example 16

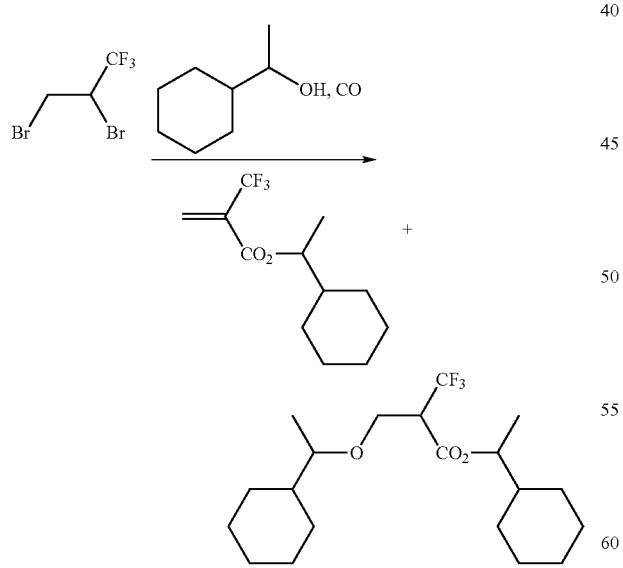

An autoclave was charged with 2,3-dibromo-1,1,1-trifluoropropane (0.2559 g, 1.0 mmol), 1-cyclohexylethanol (0.154 g, 1.2 mmol), triethylamine (0.202 g, 2.0 mmol), sodium t-butoxide (0.0192 g, 0.2 mmol), dichlorobis(triphenylphosphine)palladium(II) (0.0070 g, 0.01 mmol), and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 1-cyclohexylethyl ester was obtained with a yield of 75.0% on the basis of 2,3-dibromo-1,1,1-trifluoropropane.

2-trifluoromethyl acrylic acid 1-cyclohexylethyl ester
$^{19}$F—NMR (250 MHz, CDCl$_3$, δ ppm): −65.7 (t, J=1.37 Hz)
GC-MS MS (CI): m/z 249 (M$^+$−1)

Comparative Example 13

An autoclave was charged with 2,3-dibromo-1,1,1-trifluoropropane (0.2559 g, 1.0 mmol), 1-cyclohexyl ethanol (0.154 g, 1.2 mmol), triethylamine (0.223 g, 2.2 mmol), dichlorobis (triphenylphosphine)palladium(II) (0.0070 g, 0.01 mmol), and toluene (2.0 mL), which were stirred at 120° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a 19F—NMR integration value revealed that 2-trifluoromethyl acrylic acid 1-cyclohexyl ethyl ester was obtained with a yield of 61.5% on the basis of 2,3-dibromo-1,1,1-trifluoropropane. Also 5.9% of 3-(1-cyclohexylethyloxy)-2-(trifluoromethyl)propionic acid 1-cyclohexylethyl ester was obtained.

3-(1-cyclohexylethyloxy)-2-(trifluoromethyl)propionic acid 1-cyclohexylethyl ester
$^{19}$F—NMR (250 MHz, CDCl$_3$, δ ppm): −66.55 (d, J=8.52 Hz), −66.62 (d, J=8.52 Hz), −66.63 (d, J=8.61 Hz), −66.68 (d, J=8.59 Hz)

Example 17

An autoclave was charged with 2,3-dibromo-1,1,1-trifluoropropane (0.2559 g, 1.0 mmol), 1-cyclohexyl ethanol (0.154 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and toluene (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 1-cyclohexylethyl ester was obtained with a yield of 74.2% on the basis of 2,3-dibromo-1,1,1-trifluoropropane. Also 1.9% of 3-(1-cyclohexylethyloxy)-2-(trifluoromethyl)propionic acid 1-cyclohexylethyl ester was obtained.

Example 18

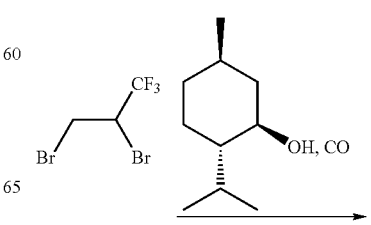

-continued

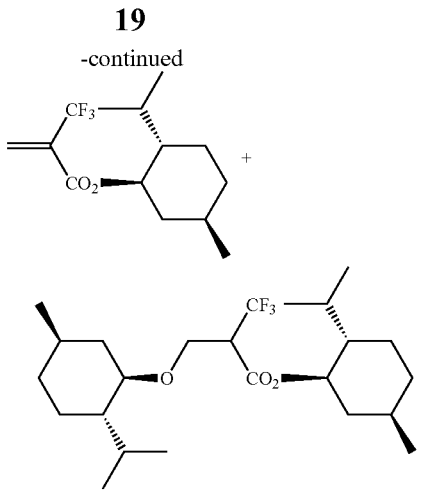

An autoclave was charged with 2,3-dibromo-1,1,1-trifluoropropane (0.2559 g, 1.0 mmol), 1-menthol (0.188 g, 1.2 mmol), triethylamine (0.202 g, 2.0 mmol), 60%-sodium hydride (0.0080 g, 0.2 mmol), dichlorobis(triphenylphosphine)palladium(II) (0.0070 g, 0.01 mmol), and toluene (2.0 mL), which were then stirred at 120° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid 1-menthyl ester was obtained with a yield of 73.2% on the basis of 2,3-dibromo-1,1,1-trifluoropropane. Also 1.0% of 3-(1-menthyloxy)-2-(trifluoromethyl)propionic acid 1-menthyl ester was obtained.

2-trifluoromethyl acrylic acid 1-menthyl ester
$^{19}F$—NMR (250 MHz, CDCl$_3$, δ ppm): −65.6 (t, J=1.48 Hz)

3-(1-menthyloxy)-2-(trifluoromethyl)propionic acid 1-menthyl ester
$^{19}F$—NMR (250 MHz, CDCl$_3$, δ ppm): −66.53 (d, J=8.53 Hz), −66.59 (d, J=8.58 Hz)

Comparative Example 14

An autoclave was charged with 2,3-dibromo-1,1,1-trifluoropropane (0.2559 g, 1.0 mmol), 1-menthol (0.188 g, 1.2 mmol), triethylamine (0.223 g, 2.2 mmol), dichlorobis(triphenylphosphine)palladium(II) (0.0070 g, 0.01 mmol), and toluene (2.0 mL), which were then stirred at 120° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid 1-menthyl ester was obtained with a yield of 43.1% on the basis of 2,3-dibromo-1,1,1-trifluoropropane. Also 6.7% of 3-(1-menthyloxy)-2-(trifluoromethyl)propionic acid 1-menthyl ester was obtained.

Example 19

An autoclave was charged with 2,3-dibromo-1,1,1-trifluoropropane (0.2559 g, 1.0 mmol), 1-menthol (0.188 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid 1-menthyl ester was obtained with a yield of 88.3% on the basis of 2,3-dibromo-1,1,1-trifluoropropane.

Example 20

An autoclave was charged with 2,3-dibromo-1,1,1-trifluoropropane (0.2559 g, 1.0 mmol), 1-menthol (0.188 g, 1.2 mmol), triethylamine (0.202 g, 2.0 mmol), lithium carbonate (0.0074 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid 1-menthyl ester was obtained with a yield of 90.4% on the basis of 2,3-dibromo-1,1,1-trifluoropropane.

Example 21

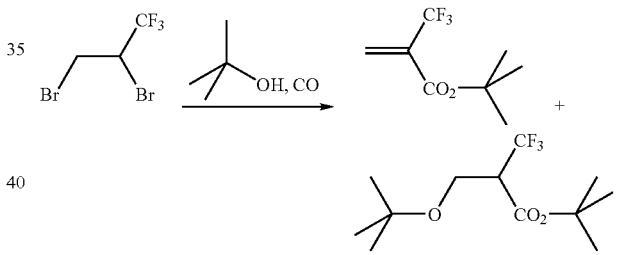

An autoclave was charged with 2,3-dibromo-1,1,1-trifluoropropane (0.2559 g, 1.0 mmol), t-butyl alcohol (0.111 g, 1.5 mmol), triethylamine (0.202 g, 2.0 mmol), sodium t-butoxide (0.0192 g, 0.2 mmol), dichlorobis(triphenylphosphine)palladium(II) (0.0070 g, 0.01 mmol), and toluene (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}F$—NMR integration value revealed that 2-trifluoromethyl acrylic acid t-butyl ester was obtained with a yield of 81.1% on the basis of 2,3-dibromo-1,1,1-trifluoropropane.

2-trifluoromethyl acrylic acid t-butyl ester
$^{19}F$—NMR (250 MHz, CDCl$_3$, δ ppm): −65.8 (t, J=1.41 Hz)
GC-MS MS (CI): m/z 197 (M$^+$+1)

Comparative Example 15

An autoclave was charged with 2,3-dibromo-1,1,1-trifluoropropane (0.2559 g, 1.0 mmol), t-butyl alcohol (0.089 g, 1.2 mmol), triethylamine (0.223 g, 2.2 mmol), dichlorobis(triphenylphosphine)palladium(II) (0.0070 g, 0.01 mmol), and toluene (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid t-butyl ester was obtained with a yield of 24.8% on the basis of 2,3-dibromo-1,1,1-trifluoropropane. Also 4.6% of 3-(t-butyloxy)-2-(trifluoromethyl)propionic acid t-butyl ester was obtained.

3-(t-butyloxy)-2-(trifluoromethyl)propionic acid t-butyl ester $^{19}$F—NMR (250 MHz, CDCl$_3$, δ ppm): −66.9 (d, J=8.61 Hz)

Example 22

An autoclave was charged with 2,3-dibromo-1,1,1-trifluoropropane (0.2559 g, 1.0 mmol), t-butyl alcohol (0.111 g, 1.5 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid t-butyl ester was obtained with a yield of 80.6% on the basis of 2,3-dibromo-1,1,1-trifluoropropane.

Example 23

An autoclave was charged with 2,3-dibromo-1,1,1-trifluoropropane (0.2559 g, 1.0 mmol), t-butyl alcohol (0.089 g, 1.2 mmol), triethylamine (0.202 g, 2.0 mmol), lithium carbonate (0.0074 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid t-butyl ester was obtained with a yield of 82.2% on the basis of 2,3-dibromo-1,1,1-trifluoropropane.

Example 24

An autoclave was charged with 2,3-dibromo-1,1,1-trifluoropropane (0.2559 g, 1.0 mmol), t-butyl alcohol (0.089 g, 1.2 mmol), triethylamine (0.202 g, 2.0 mmol), lithium carbonate (0.0148 g, 0.2 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid t-butyl ester was obtained with a yield of 84.9% on the basis of 2,3-dibromo-1,1,1-trifluoropropane.

Example 25

An autoclave was charged with 2,3-dibromo-1,1,1-trifluoropropane (0.2559 g, 1.0 mmol), t-butyl alcohol (0.089 g, 1.2 mmol), triethylamine (0.202 g, 2.0 mmol), lithium carbonate (0.0369 g, 0.5 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid t-butyl ester was obtained with a yield of 84.4% on the basis of 2,3-dibromo-1,1,1-trifluoropropane.

Example 26

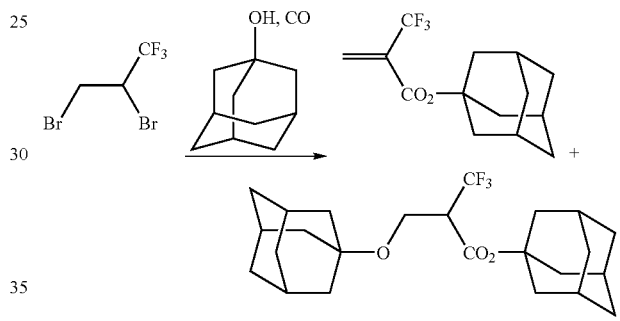

An autoclave was charged with 2,3-dibromo-1,1,1-trifluoropropane (0.2559 g, 1.0 mmol), 1-adamantanol (0.183 g, 1.2 mmol), triethylamine (0.202 g, 2.0 mmol), 60%-sodium hydride (0.0080 g, 0.2 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 1-admantyl ester was obtained with a yield of 87.9% on the basis of 2,3-dibromo-1,1,1-trifluoropropane.

2-trifluoromethyl acrylic acid 1-admantyl ester $^{19}$F-NMR (250 MHz, CDCl$_3$, δ ppm): −65.5 (t, J=1.48 Hz)

Comparative Example 16

An autoclave was charged with 2,3-dibromo-1,1,1-trifluoropropane (0.2559 g, 1.0 mmol), 1-adamantanol (0.183 g, 1.2 mmol), triethylamine (0.223 g, 2.2 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—

NMR integration value revealed that 2-trifluoromethyl acrylic acid 1-admantyl ester was obtained with a yield of 23.7% on the basis of 2,3-dibromo-1,1,1-trifluoropropane. Also, 0.6% of 3-(1-adamantyloxy)-2-(trifluoromethyl)propionic acid 1-admantyl ester was obtained.

3-(1-adamantyloxy)-2-(trifluoromethyl)propionic acid 1-admantyl ester $^{19}$F—NMR (250 MHz, CDCl$_3$, δ ppm): −66.6 (d, J=8.60 Hz)

Example 27

An autoclave was charged with 2,3-dibromo-1,1,1-trifluoropropane (0.2559 g, 1.0 mmol), 1-adamantanol (0.183 g, 1.2 mmol), triethylamine (0.202 g, 2.0 mmol), lithium carbonate (0.0074 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 1-admantyl ester was obtained with a yield of 89.0% on the basis of 2,3-dibromo-1,1,1-trifluoropropane.

Example 28

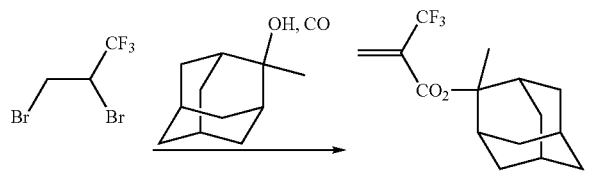

An autoclave was charged with 2,3-dibromo-1,1,1-trifluoropropane (0.2559 g, 1.0 mmol), 2-methyl-2-adamantanol (0.249 g, 1.5 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methyl-2-adamantyl ester was obtained with a yield of 70.5% on the basis of 2,3-dibromo-1,1,1-trifluoropropane.

2-trifluoromethyl acrylic acid 2-methyl-2-adamantyl ester $^{19}$F—NMR (250 MHz, CDCl$_3$, δ ppm): −65.5 (t, J=1.53 Hz)

Comparative Example 17

An autoclave was charged with 2,3-dibromo-1,1,1-trifluoropropane (0.2559 g, 1.0 mmol), 2-methyl-2-adamantanol (0.332 g, 2.0 mmol), triethylamine (0.223 g, 2.2 mmol), dichlorobis(triphenylphosphine)palladium(II) (0.0070 g, 0.01 mmol), and tetrahydrofuran (2.0 mL), which were then stirred at 120° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methyl-2-adamantyl ester was obtained with a yield of 19.1% on the basis of 2,3-dibromo-1,1,1-trifluoropropane.

Example 29

An autoclave was charged with 2,3-dibromo-1,1,1-trifluoropropane (0.2559 g, 1.0 mmol), 2-methyl-2-adamantanol (0.249 g, 1.5 mmol), triethylamine (0.202 g, 2.0 mmol), lithium carbonate (0.0369 g, 0.5 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methyl-2-adamantyl ester was obtained with a yield of 91.1% on the basis of 2,3-dibromo-1,1,1-trifluoropropane.

Example 30

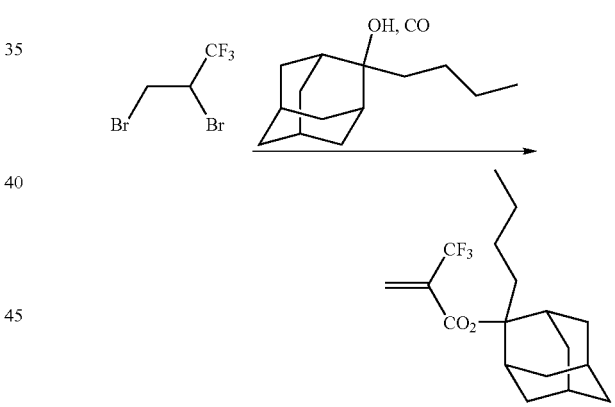

An autoclave was charged with 2,3-dibromo-1,1,1-trifluoropropane (0.2559 g, 1.0 mmol), 2-butyl-2-adamantanol (0.313 g, 1.5 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-butyl-2-adamantyl ester was obtained with a yield of 41.9% on the basis of 2,3-dibromo-1,1,1-trifluoropropane.

2-trifluoromethyl acrylic acid 2-butyl-2-adamantyl ester $^{19}$F—NMR (250 MHz, CDCl$_3$, δ ppm): −65.6 (t, J=1.45 Hz)

Example 31

An autoclave was charged with 2,3-dibromo-1,1,1-trifluoropropane (0.2559 g, 1.0 mmol), 2-butyl-2-adamantanol (0.313 g, 1.5 mmol), triethylamine (0.202 g, 2.0 mmol), lithium carbonate (0.0369 g, 0.5 mmol), dichlorobis(triphenylphosphine)palladium(II) (0.0070 g, 0.01 mmol), and cyclopentylmethyl ether (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F-NMR integration value revealed that 2-trifluoromethyl acrylic acid 2-butyl-2-adamantyl ester was obtained with a yield of 74.5% on the basis of 2,3-dibromo-1,1,1-trifluoropropane.

Example 32

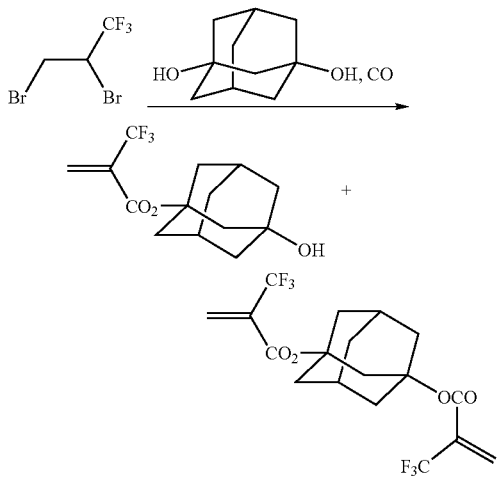

An autoclave was charged with 2,3-dibromo-1,1,1-trifluoropropane (0.2559 g, 1.0 mmol), 1,3-adamantane diol (0.202 g, 1.2 mmol), triethylamine (0.202 g, 2.0 mmol), 60%-sodium hydride (0.0080 g, 0.2 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that mono(2-trifluoromethyl) acrylic acid 1,3-adamantanediyl ester was obtained with a yield of 62.8% on the basis of 2,3-dibromo-1,1,1-trifluoropropane. Also 21.7% (0.108 mmol) of bis(2-trifluoromethyl) acrylic acid 1,3-adamantanediyl ester was obtained.

Mono(2-trifluoromethyl) acrylic acid 1,3-adamantadiyl ester $^{19}$F—NMR (250 MHz, CDCl$_3$, δ ppm): −65.81 (t, J=1.50 Hz)

bis(2-trifluoromethyl) acrylic acid 1,3-adamantadiyl ester $^{19}$F—NMR (250 MHz, CDCl$_3$, δ ppm): −65.80 (t, J=1.48 Hz)

Comparative Example 18

An autoclave was charged with 2,3-dibromo-1,1,1-trifluoropropane (0.2559 g, 1.0 mmol), 1,3-adamantane diol (0.168 g, 1.0 mmol), triethylamine (0.223 g, 2.2 mmol), dichlorobis (triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that mono(2-trifluoromethyl) acrylic acid 1,3-adamantanediyl ester was obtained with a yield of 18.7% on the basis of 2,3-dibromo-1,1,1-trifluoropropane. Also 7.3% (0.036 mmol) of bis(2-trifluoromethyl) acrylic acid 1,3-adamantanediyl ester was obtained.

Example 33

An autoclave was charged with 2,3-dibromo-1,1,1-trifluoropropane (0.2559 g, 1.0 mmol), 1,3-adamantane diol (0.202 g, 1.2 mmol), triethylamine (0.202 g, 2.0 mmol), sodium carbonate (0.0106 g, 0.1 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that mono(2-trifluoromethyl) acrylic acid 1,3-adamantanediyl ester was obtained with a yield of 67.1% on the basis of 2,3-dibromo-1,1,1-trifluoropropane. Also 20.4% (0.102 mmol) of bis(2-trifluoromethyl) acrylic acid 1,3-adamantanediyl ester was obtained.

Example 34

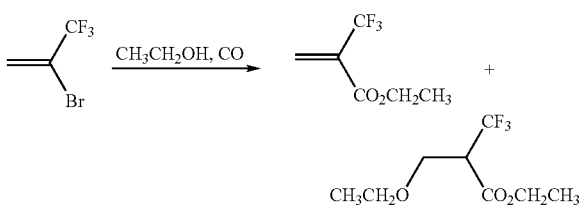

An autoclave was charged with 2-bromo-3,3,3-trifluoropropene (0.175 g, 1.0 mmol), ethanol (0.055 g, 1.2 mmol), triethylamine (0.101 g, 1.0 mmol), lithium carbonate (0.0074 g, 0.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid ethyl ester was obtained with a yield of 82.0% on the basis of 2-bromo-3,3,3-trifluoropropene. Also 3.3% of 3-ethoxy-2-(trifluoromethyl)propionic acid ethyl ester was obtained.

Comparative Example 19

An autoclave was charged with 2-bromo-3,3,3-trifluoropropene (0.175 g, 1.0 mmol), ethanol (0.055 g, 1.2 mmol), triethylamine (0.111 g, 1.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid ethyl ester was obtained with a yield of 62.1% on the basis of 2-bromo-3,3,3-trifluoropropene. Also 16.7% of 3-ethoxy-2-(trifluoromethyl)propionic acid ethyl ester was obtained.

Example 35

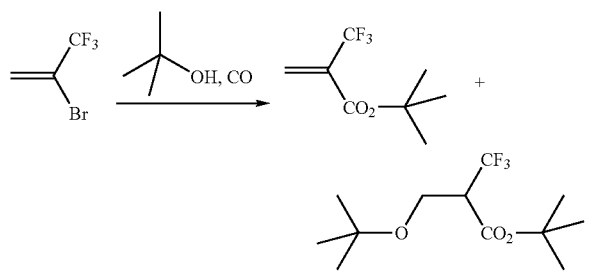

An autoclave was charged with 2-bromo-3,3,3-trifluoropropene (0.175 g, 1.0 mmol), t-butyl alcohol (0.089 g, 1.2 mmol), triethylamine (0.101 g, 1.0 mmol), lithium carbonate (0.0148 g, 0.2 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid t-butyl ester was obtained with a yield of 75.7% on the basis of 2-bromo-3,3,3-trifluoropropene.

Comparative Example 20

An autoclave was charged with 2-bromo-3,3,3-trifluoropropene (0.175 g, 1.0 mmol), t-butyl alcohol (0.089 g, 1.2 mmol), triethylamine (0.111 g, 1.1 mmol), dichlorobis(triphenylphosphine)palladium(II) (0.0070 g, 0.01 mmol), and tetrahydrofuran (2.0 mL), which were then stirred at 100° C. for 5 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid t-butyl ester was obtained with a yield of 12.6% on the basis of 2-bromo-3,3,3-trifluoropropene.

Example 36

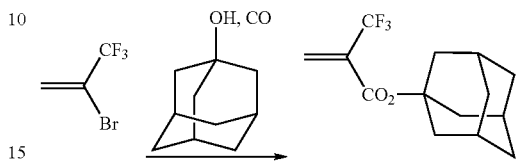

An autoclave was charged with 2-bromo-3,3,3-trifluoropropene (0.175 g, 1.0 mmol), 1-adamantanol (0.183 g, 1.2 mmol), triethylamine (0.101 g, 1.0 mmol), lithium carbonate (0.0074 g, 0.1 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 1-admantyl ester was obtained with a yield of 80.2% on the basis of 2-bromo-3,3,3-trifluoropropene.

Comparative Example 21

An autoclave was charged with 2-bromo-3,3,3-trifluoropropene (0.175 g, 1.0 mmol), 1-adamantanol (0.183 g, 1.2 mmol), triethylamine (0.111 g, 1.1 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-adamantyl ester was obtained with a yield of 13.9% on the basis of 1-bromo-3,3,3-trifluoropropene.

Example 37

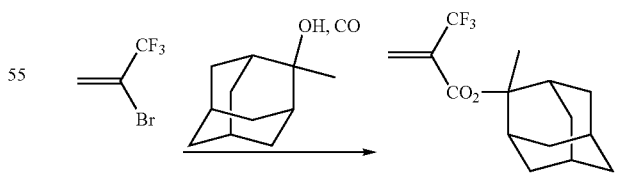

An autoclave was charged with 2-bromo-3,3,3-trifluoropropene (0.175 g, 1.0 mmol), 2-methyl-2-adamantanol (0.200 g, 1.2 mmol), triethylamine (0.101 g, 1.0 mmol), lithium carbonate (0.0369 g, 0.5 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG).

After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methyl-2-adamantyl ester was obtained with a yield of 79.6% on the basis of 2-bromo-3,3,3-trifluoropropene.

Comparative Example 22

An autoclave was charged with 2-bromo-3,3,3-trifluoropropene (0.175 g, 1.0 mmol), 2-methyl-2-adamantanol (0.200 g, 1.2 mmol), triethylamine (0.111 g, 1.1 mmol), dichlorobis(triphenylphosphine)palladium(II) (0.0070 g, 0.01 mmol), and tetrahydrofuran (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-methyl-2-adamantyl ester was obtained with a yield of 4.1% on the basis of 2-bromo-3,3,3-trifluoropropene.

Example 38

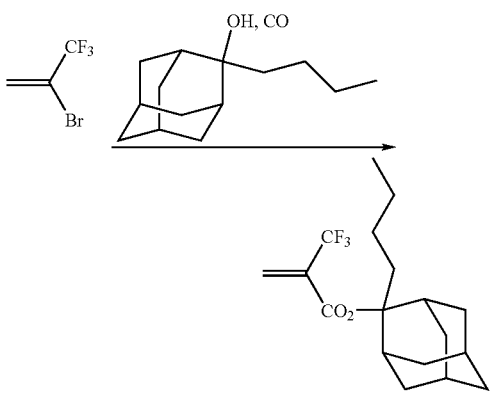

An autoclave was charged with 2-bromo-3,3,3-trifluoropropene (0.175 g, 1.0 mmol), 2-butyl-2-adamantanol (0.250 g, 1.2 mmol), triethylamine (0.101 g, 1.0 mmol), lithium carbonate (0.0148 g, 0.2 mmol), dichlorobis(triphenylphosphine)palladium(II) (0.0070 g, 0.01 mmol), and cyclopentylmethyl ether (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F-NMR integration value revealed that 2-trifluoromethyl acrylic acid 2-butyl-2-adamantyl ester was obtained with a yield of 70.1% on the basis of 2-bromo-3,3,3-trifluoropropene.

Comparative Example 23

An autoclave was charged with 2-bromo-3,3,3-trifluoropropene (0.175 g, 1.0 mmol), 2-butyl-2-adamantanol (0.250 g, 1.2 mmol), triethylamine (0.111 g, 1.1 mmol), dichlorobis(triphenylphosphine)palladium(II) (0.0070 g, 0.01 mmol), and cyclopentylmethyl ether (2.0 mL), which were then stirred at 100° C. for 15 hours after introducing carbon monoxide (1.0 MPaG). After the end of the reaction, the autoclave was cooled, ventilated, and added with benzotrifluoride as an internal standard substance, followed by stirring and leaving still for a while to let a salt precipitate. Quantification using a $^{19}$F—NMR integration value revealed that 2-trifluoromethyl acrylic acid 2-butyl-2-adamantyl ester was obtained with a yield of 4.2% on the basis of 2-bromo-3,3,3-trifluoropropene.

INDUSTRIAL APPLICABILITY

The present invention provides a simple and highly versatile and selective process for producing a fluorine-containing acrylic acid ester which is a useful compound having wide applications in materials for pharmaceuticals and functional polymers.

The invention claimed is:

1. A process for producing a fluorine-containing acrylic acid ester represented by the general formula (IV):

(wherein, Rf represents a perfluoroalkyl group and R represents an unsubstituted or substituted alkyl group), which comprises reacting 1-bromo-1-perfluoroalkylethene represented by the general formula (I):

(wherein Rf is as defined above), or 1,2-dibromo-1-perfluoroalkylethane represented by the general formula (II):

(wherein Rf is as defined above) with an alcohol represented by the general formula (III):

(wherein R is as defined above) in the presence of a palladium catalyst, carbon monoxide, and two or more bases, wherein at least one of the bases is an inorganic base, an inorganic salt, or an organic metal, and at least one of the bases is an amine.

2. The process according to claim 1, wherein the inorganic base, the inorganic salt, or the organic metal is used in a molar ratio of 0.001 to 1, relative to the compound represented by the general formula (I) or (II).

3. The process according to claim 1, wherein the alcohol is a straight, branched, or cyclic aliphatic alcohol.

4. The process according to claim 1, wherein the amine is used in a molar ratio of at least 1, relative to the compound represented by the general formula (I) or (II).

5. The process according to claim 2, wherein the alcohol is a straight, branched, or cyclic aliphatic alcohol.

* * * * *